Un
ited States Patent [19]

Ni

[11] Patent Number: 4,916,163

[45] Date of Patent: Apr. 10, 1990

[54] SPRAY-DRIED LACTOSE FORMULATION OF MICRONIZED GLYBURIDE

[75] Inventor: Philip F. Ni, Texas Township, Mich.

[73] Assignee: The Upjohn Company, Kalamazoo, Mich.

[21] Appl. No.: 741,241

[22] Filed: Jun. 4, 1985

[51] Int. Cl.$^4$ ............................................. A61K 31/17
[52] U.S. Cl. .................................... 514/593; 514/866
[58] Field of Search ................................ 514/593, 866

[56] References Cited

U.S. PATENT DOCUMENTS

| | | | |
|---|---|---|---|
| 3,426,067 | 2/1969 | Weber et al. | 260/553 |
| 3,454,635 | 7/1969 | Weber et al. | 260/553 |
| 3,507,954 | 4/1970 | Weber et al. | 424/321 |
| 3,507,961 | 4/1970 | Weber et al. | 424/275 |
| 3,932,658 | 1/1976 | Weber et al. | 514/593 |
| 3,979,520 | 9/1976 | Rothe et al. | 424/321 |
| 4,060,634 | 11/1977 | Rothe et al. | 424/321 |
| 4,446,129 | 5/1984 | Sawada | 424/94 |
| 4,562,071 | 12/1985 | Tokumori et al. | 424/94 |

*Primary Examiner*—Frederick E. Waddell
*Attorney, Agent, or Firm*—Robert A. Armitage

[57] ABSTRACT

An improved, more bioavailable formulation of glyburide is provided which consists preponderantly by weight of spray-dried lactose is described. This formulation utililzes micronized glyburide, but is more economically manufacatured than heretofore known micronized glyburide formulations.

4 Claims, No Drawings

SPRAY-DRIED LACTOSE FORMULATION OF MICRONIZED GLYBURIDE

BACKGROUND OF THE INVENTION

The present invention provides a novel formulation of glyburide, N-[4-($\beta$-[2-methoxy-5-chloro-benzamido]-ethyl)-benzenesulfonyl]-N'-cyclohexyl-urea, an anti-diabetic sulfonylurea. See The Merck Index, Tenth Edition, p. 642. The present invention further provides such formulation in a more readily manufacturable and bioavailable form than was heretofore attained. Glyburide in various formulations is available for the treatment of Type II (adult-onset) diabetes mellitus. It is effective in reducing serum glucose concentrations, effectuating control of the disease in those situaitons where non-pharmaceutical means (e.g., diet and lifestyle changes) are inadequate. See U.S. Pat. Nos. 3,426,067, 3,454,635, 3,507,961, and 3,507,954.

Subsequent to the discovery of glyburide itself, more bioavailable glyburide compositions became available as described in U.S. Pat. Nos. 3,979,520 and 4,060,634. These patents describe the use of micronized or high surface area, e.g., 3 to 10 $m^2/g$, glyburide in combination with various pharmaceutically acceptable excipients to obtain enhanced bioavailability. More particularly, these patents describe the use of a wetting agent in the glyburide compositions present at 5 to 10 times the weight of glyburide. The patents specifically exemplify the use of polyoxyethylene stearate as the preferred wetting agent.

In order to obtain the more bioavailable formulation as described in the above patents, the glyburide and the pharmaceutical excipients need to be granulated, following which the resulting mixture must be dried and milled before compressing into tablets. These activities require intensive use of manpower and energy in order to obtain a highly bioavailable composition.

INFORMATION DISCLOSURE

Glyburide and certain micronized glyburide anti-diabetic pharmaceutical compositions are known. See the references cited above.

SUMMARY OF THE INVENTION

The present invention particularly provides:

In a micronized glyburide anti-diabetic pharmaceutical composition as a unit dose, containing one or more pharmaceutically acceptable excipients, the improvement which comprises:
spray-dried lactose as the preponderant excipient in said composition, being present therein at about not less than seventy percent (70%) by weight of the final composition.

A typical pharmaceutical composition in accordance with the present invention is a compressed tablet which would contain:

| | |
|---|---|
| Micronized glyburide (ca. 5 $m^2/g$) | 5.25 mg |
| Spray-dried lactose | 140.00 mg |
| Corn starch | 28.60 mg |
| Silicon dioxide | 1.00 mg |
| Magnesium stearate | 0.75 mg. |

The spray-dried lactose content of this formulation would represent approximately 80% by weight of the total formulation.

Compositions in accordance with the present invention are most typically composed of multiple excipients in addition to the glyburide and the spray-dried lactose, as in the composition above. These excipients include tablet disintegrants, such as the corn starch, glidants, such as the silicon dioxide, and lubricants such as the magnesium stearate. Ordinarily these compositions contain minor amounts by weight of glidants and lubricants, e.g., each two percent (2%) or less by weight. Tablet disintegrants are optionally present, and, if present, are included in sufficient amounts to assure that the tablet disintegrates upon ingestion. According materials, such as corn starch are advantageous employed at concentrations of from about zero to about 30 percent by weight of the composition.

Each compressed tablet contains an appropriate unit dose of glyburide. Accordingly, the tablet would contain on the order of from 1 to about 6 mg of glyburide, although compressed tablets containing greater or lesser amounts of active ingredient could be readily prepared. The glyburide employed in these compositions must be micronized and is characterized by a surface area of at least 3 $m^2/g$. Such material is known in the art and its preparation is described in the patents referenced above.

Critical to the success of the present composition is the employment of spray-dried lactose as the preponderant component by weight of the resulting composition. Most preferably the spray-dried lactose will represent at least about 80% by weight of the resulting tablet. Spray-dried lactose can be employed as commercially available. For example, Foremost Spray-dried Lactose #315 or #316 is highly useful in the manufacture of compositions in accordance with the present invention. The particle size of the lactose must be sufficiently large to permit a mixture of the lactose and the glyburide to be free flowing. Selection of a spray-dried lactose product of insufficient particle size will result in a mixture which aggregates and is otherwise difficult to process. Similarly, the spray-dried lactose must contain a relatively narrow distribution of particle sizes. Preferably, the spray-dried lactose has the following characteristics:

not less than 100% passes through a #40 sieve;
not less than 1% is retained on a #80 sieve;
not more than 20% is retained on a #80 sieve;
not less than 10% is retained on a #140 sieve; and
not more than 60% passes through a #200 sieve.

Compositions of the present invention are manufactured readily by the following processing steps:
(1) Combine the micronized glyburide with the spray-dried lactose in a manner to ensure complete dispersion;
(2) Combine the product of step (1) above with a combination of all remaining excipients except the lubricant;
(3) Following addition of the lubricant to the product of step (2) above, compress the resulting homogeneous mixture into a tableting die of the appropriate size to yield tablets of the desired strength.

As is apparent from the processing steps outlined above, the present invention yields a formulation which does not require wet granulation and drying prior to compression and further avoids the need for sizing or milling the granulated material. Hence the present invention is surprisingly and unexpectedly more economical to manufacture than the micronized formulations heretofore known, e.g., see U.S. Pat. No. 4,060,634.

DESCRIPTION OF THE PREFERRED EMBODIMENTS

The advantageous of the present invention in view of compositions heretofore available is more readily understood by the following example:

EXAMPLE

Comparative bioavailability of MICRONASE (5 mg, glyburide, Upjohn) Spray-dried Lactose Formulation (3.5 mg, glyburide) and Spray-dried Lactose Formulation (3 mg, glyburide).

Serum glyburide concentrations are measured following oral administration to twenty-eight normal healthy adults of glyburide compressed tablets.

Three different formulations are employed as follows:

I. MICRONASE (5 mg, glyburide, Upjohn) as commercially available in the United States.

II. Spray-dried Lactose Formulation (3.5 mg, glyburide) as prepared in accordance the present invention.

III. Spray-dried Lactose Formulation (3.0 mg, glyburide) as prepared in accordance with the present invention.

The following results are observed:

1. Mean bioavailability parameters are evaluated and indicate that formulation III is closer than formulation II to the commercially available formulation I in terms of bioavailability.
2. Formulations II and III are more rapidly absorbed than formulation I.

The following parameters relating to bioavailability are determined:

|  | I | II | III |
|---|---|---|---|
| Maximal Concentration (ng/ml) | 121 | 172 | 141 |
| Aggregate Absorption (ng-hr/ml) | 640 | 701 | 582 |
| Time to Maximum Concentration (hr) | 3.3 | 2.4 | 2.4 |

The foregoing data indicate that the present invention provides a surprisingly and unexpectedly more bioavailable formulation than that currently marketed and is surprisingly and unexpectedly more convenient and economical to manufacture than alternative formulations exhibiting enhanced bioavailability.

I claim:

1. In an micronized glyburide anti-diabetic pharmaceutical composition as a unit dose, containing one or more pharmaceutically acceptable excipients, the improvement which comprises:
    spray-dried lactose as the preponderant excipient in said composition, being present therein at about not less that seventy percent (70%) by weight of the final composition.
2. The improvement according to claim 1 wherein the micronized glyburide has a surface area of about 5 $m^2/g$.
3. The improvement according to claim 1 wherein the excipients comprise a glidant, lubricant and disintegrant.
4. The improvement according to claim 1 wherein the excipients comprise corn starch, silicon dioxide, and magnesium stearate.

* * * * *

UNITED STATES PATENT AND TRADEMARK OFFICE
CERTIFICATE OF CORRECTION

PATENT NO. : 4,916,163
DATED : April 10, 1990
INVENTOR(S) : Ashok C. Shah et al

It is certified that error appears in the above-indentified patent and that said Letters Patent is hereby corrected as shown below:

On the title page, item [75] the names of the inventors are as shown below:
Ashok C. Shah, Phillip F. Ni, Richard P. Poska and Jessie F. Glascock, Jr.

Signed and Sealed this

Twentieth Day of February, 1996

Attest:

BRUCE LEHMAN

*Attesting Officer*    *Commissioner of Patents and Trademarks*